US008840571B2

United States Patent
Egorov et al.

(10) Patent No.: US 8,840,571 B2
(45) Date of Patent: Sep. 23, 2014

(54) METHOD AND DEVICE FOR MEASURING TACTILE PROFILE OF VAGINA

(71) Applicants: Vladimir Egorov, Princeton, NJ (US); Armen P. Sarvazyan, Lambertville, NJ (US)

(72) Inventors: Vladimir Egorov, Princeton, NJ (US); Armen P. Sarvazyan, Lambertville, NJ (US)

(73) Assignee: Artann Laboratories Inc., Trenton, NJ (US)

( * ) Notice: Subject to any disclaimer, the term of this patent is extended or adjusted under 35 U.S.C. 154(b) by 93 days.

(21) Appl. No.: 13/756,788

(22) Filed: Feb. 1, 2013

(65) Prior Publication Data
US 2013/0144191 A1 Jun. 6, 2013

Related U.S. Application Data

(60) Continuation-in-part of application No. 13/439,165, filed on Apr. 4, 2012, now Pat. No. 8,419,659, which is a division of application No. 13/083,494, filed on Apr. 8, 2011, now Pat. No. 8,187,208, which is a continuation-in-part of application No. 12/874,583, filed on Sep. 2, 2010, now Pat. No. 8,052,622.

(60) Provisional application No. 61/617,555, filed on Mar. 29, 2012, provisional application No. 61/239,087, filed on Sep. 2, 2009.

(51) Int. Cl.
*A61B 5/117* (2006.01)
*A61B 5/103* (2006.01)
*A61B 5/00* (2006.01)
*A61B 5/22* (2006.01)

(52) U.S. Cl.
CPC ............ *A61B 5/227* (2013.01); *A61B 5/4337* (2013.01); *A61B 5/6847* (2013.01)
USPC ...................................................... 600/591

(58) Field of Classification Search
CPC ..... A61B 5/227; A61B 5/4337; A61B 5/6847
USPC ............ 600/587, 591, 462, 438, 471; 707/1; 606/228
See application file for complete search history.

(56) References Cited

U.S. PATENT DOCUMENTS

| 6,741,895 B1 | 5/2004 | Gafni |
| 2011/0196263 A1 | 8/2011 | Egorov |
| 2011/0208178 A1 | 8/2011 | Truckai |

*Primary Examiner* — Brian Szmal
(74) *Attorney, Agent, or Firm* — Boris Leschinsky

(57) ABSTRACT

Transvaginal probes equipped with tactile sensors are configured for placement into vagina to record tactile response during insertion, acquire static tactile pattern from vaginal wall after the insertion is complete, and acquire dynamic tactile patterns during probe motion as well as recording dynamic tactile response during contraction of vaginal muscle. The acquired and recorded tactile data are transmitted to a data processor for composing tactile profile of vagina and visually presenting thereof on a display. Elasticity profile of vaginal tissue is calculated from the tactile response recorded from different parts of the probe during its insertion, from the static pressure pattern and from the dynamic tactile pattern. Pelvic floor muscle strength is defined as a contact pressure increase detected on fixed probe surface under the muscle contraction. Tactile profile of vagina is determined using the static tactile pattern, the elasticity profile and pelvic floor muscle strength. The data processor provides a comparative analysis of the tactile profile with a variety of vaginal tactile profiles recorded for a given population with known clinical conditions so as to assist in diagnosing a disease.

18 Claims, 13 Drawing Sheets

METHOD AND DEVICE FOR MEASURING TACTILE PROFILE OF VAGINA

CROSS-REFERENCE TO RELATED APPLICATIONS

This patent application claims a priority benefit from and is a non-provisional filing of the US Provisional Patent Application No. 61/617,555 filed 29 Mar. 2012 by the same inventors and with the same title.

This patent application is also a continuation-in-part of a U.S. patent application Ser. No. 13/439,165 filed 4 Apr. 2012 and entitled "METHODS FOR ASSESSMENT OF IMPROVEMENTS IN PELVIC ORGAN CONDITIONS AFTER AN INTERVENTIONAL PROCEDURE", which in turn is a divisional of U.S. patent application Ser. No. 13/083,494 filed 8 Apr. 2011 entitled "Methods for assessment of pelvic organ conditions affecting the vagina", which in turn is a continuation-in-part of U.S. patent application Ser. No. 12/874,583 filed 2 Sep. 2010 entitled "Methods for characterizing vaginal tissue elasticity", now U.S. Pat. No. 8,052,622, which in turn claims a priority benefit from a U.S. Provisional Patent Application No. 61/239,087 filed 2 Sep. 2009 entitled "Methods of using a vaginal tactile imager for pelvic organ prolapse characterization, including that after a reconstructive surgery", all of which are incorporated herein in their respective entireties by reference.

GOVERNMENT-SUPPORTED RESEARCH

This invention was made with the US Government support under grant No. AG034714 awarded by the National Institute on Aging, National Institutes of Health. The Government has certain rights in this invention.

BACKGROUND OF THE INVENTION

The present invention generally relates to characterization methods for female pelvic tissues. Specifically, the invention describes methods and devices for characterizing pelvic floor support structures including vaginal tissue elasticity and muscle strength.

Various stages of pelvic organ abnormality including a pelvic organ prolapse (POP) are highly prevalent affecting at least 50% of women in the US during their lifetimes. Some loss of utero-vaginal support occurs in most adult women. POP is the leading indication for hysterectomy in postmenopausal women and accounts for 15-18% of procedures in all age-groups [Kesharvarz H, Hillis S D, Kieke B A, Marchbanks P A. Hysterectomy surveillance—United States 1994-1999. MMWR Surveill Summ 2002; 51 (5505):1-8]. Beyond the physical impact of POP, women with progressing pelvic organ abnormality score poorer on both generic and condition-specific quality-of-life scales [Jelovsek J E, Barber M D. Women seeking treatment for advanced pelvic organ abnormality have decreased body image and quality of life. Am J Obstet Gynecol. 2006; 194: 1455-61.]. In addition, about one third of sexually active women with POP report that their condition interferes with sexual function [Barber M D, Visco A G, Wyman, et al. Sexual function in women with urinary incontinence and pelvic organ abnormality. Obstet Gynecol. 2002; 99:281-9.].

Conservative treatment of pelvic floor abnormalities includes lifestyle interventions, physical therapies, pelvic floor muscle training, scheduled voiding regimens, electrical and magnetic stimulations, complementary and alternative medicines (i.e. those not considered part of the traditional biomedical model), anti-incontinence devices, supportive rings and pessaries, pads and catheters. Conservative therapies are usually low cost, and managed principally by the patient with instruction/supervision from a health professional. They differ from other forms of incontinence and prolapse management, in that they have a low risk of adverse effects and do not prejudice other subsequent treatments [Smith J H, Berghmans B, Burgio K, et al. Adult Conservative Managements. Committee 12. Incontinence. Eds: Abrams P, Cardozo L, Khoury S, Wein A. Health Publication Ltd.; 2009: 1026-1120]. There is a need in quantitative characterization of outcome of the conservative treatment of pelvic floor abnormalities.

Women with symptomatic POP who fail or decline conservative management, including pessary use and physical therapy treatment, are candidates for reconstructive surgery. The overall goal for prolapse surgery is to give the most functional repair, while preventing recurrence of the condition and minimizing complications incurred by these repairs. Recurrence is one of the barriers in surgical correction most frustrating to both the surgeon and patient. Failure rates as high as 20-40% have been cited after surgical repair, with over 50% occurring within the first three years [Clemons J L, Myers D L, Aguilar V C, Arya L A. Vaginal paravaginal repair with an AlloDerm graft. Am J Obstet Gynecol. 2003; 189(6): 1612-1618]. Since many patients with POP have inherently deficient or defective connective tissue, to minimize recurrence of POP many reconstructive surgeons have turned to the use of adjuvant materials for vaginal support. Such materials may include synthetic, allogenic, xenogenic or autologous grafts [Bako A, Dhar R. Review of synthetic mesh-related complications in pelvic floor reconstructive surgery. Int Urogynecol J Pelvic Floor Dysfunct. 2009; 20(1):103-111]. There is a need in quantitative characterization of outcome of pelvic floor reconstructive surgery.

Clinical diagnosis of vaginal abnormalities and ultimately POP involves taking a medical history and performing a manual physical examination when a physician inspects the urogenital areas and rectum for masses and indication of reduced muscle tone. The physician instructs the patient to cough, bear down or perform a Valsalva maneuver (a forceful attempt at exhalation with the mouth and nose closed) to see if and how far the vagina descends as the result of the additional abdominal pressure [Shagam J Y. Pelvic organ prolapse. Radiol Technol. 2006; 77(5):389-400].

While physical examination helps the clinician describe the extent of pelvic floor prolapse, it does not help in discerning the initial stage of abnormality development from the normal condition. Digital palpation does not provide quantitative tissue characterization to compare with normal elasticity of vaginal walls. It has poor sensitivity and is highly subjective.

Changes in the elasticity of the vaginal walls, connective support tissues, and muscles are significant factors in the development of POP. The high incidence of POP dictates the need for new effective methods of objective vaginal tissue characterization and early disease detection.

SUMMARY OF THE INVENTION

The object of the present invention is to overcome the drawbacks of the prior art and to provide novel method and device for objective characterizing of pelvic floor support structures including vaginal tissue elasticity, in particular by measuring tactile profile of vagina using tactile sensors mounted on a novel transvaginal probe.

Another object of the invention is to provide methods and devices for objective detection of pelvic organ disease or abnormality.

Another object of the invention is to provide methods and devices for objective quantitative characterization of outcome of a conservative treatment of a pelvic floor disease.

A further object of the invention is to provide methods and devices for quantitative characterization of outcome of pelvic floor reconstructive surgery.

A further object of the invention is to provide methods and devices for detecting pelvic organ disease by comparing a calculated tactile profile of a particular patient against a pool of profiles for a population with a known clinical status.

A further object of the invention is to provide methods and devices for measuring static and transitional tactile patterns of vaginal walls.

A further object of the invention is to provide methods and devices for determining vaginal muscle strength by measuring tactile response on a rigid surface of the probe during pelvic floor muscle contraction.

A further yet object of the invention is to provide methods and devices for objective diagnosis of a pelvic organ disease by comparing a calculated elasticity profile, static tactile pattern and pelvic floor muscle strength of a particular patient against respective normal values obtained from clinical data collected from a number of patients with known clinical status.

In embodiments, the method for measuring tactile profile of vagina comprises the steps of:
  recording of a tactile response from at least one of the two opposing vaginal walls during insertion of a transvaginal probe into vagina,
  recording a static tactile pattern from at least one of the two opposite vaginal walls and optionally a uterus after the probe insertion,
  calculating distribution of vaginal tissue elasticity for at least a portion or the entire vagina using static and/or transitional tactile responses from at least the front part of the transvaginal probe, and
  determining a vaginal tactile profile from the static and/or transitional tactile patterns and distribution of vaginal tissue elasticity based on the static and transitional tactile responses recorded for the same location in vagina.

In embodiments, the method for measuring tactile profile of vagina may also include a step of determining of pelvic floor muscle strength using a tactile pattern recorded during vaginal muscle contraction.

In embodiments, a transvaginal probe for measuring tactile profile of vagina includes a hand-held housing equipped with a tactile sensor array configured to simultaneously obtain tactile signals from a plurality of locations in vagina including at least a portion of one or two opposing vaginal walls such as an anterior and a posterior wall and/or a uterus. The probe is also configured to detect and communicate to the user with an indicator the position of the probe of reaching the uterus, which may be used as a reference point in composing a vaginal tactile profile. The transvaginal probe also includes a controller with a data processor for composing the vaginal tactile profile using tactile patterns and responses obtained during probe insertion into vagina. The probe is adapted to record both dynamic and static tactile patterns when it is respectively being moved or left in place.

The probe has a distal portion shaped for atraumatic insertion into vagina. This portion of the probe has a tapered front portion and optionally an adjacent extrusive portion or predetermined shape and size so as to provide the vaginal walls with a known geometrical tissue deformation upon insertion.

The transvaginal probe is further equipped with a display and optionally with an accelerometer for detecting its angle relative to the Earth horizon, which is used in measuring of vaginal transitional tactile pattern for anterior and posterior compartments, when the probe is elevated up and down relative to hymen or allowed to deform pelvic floor tissues based on its own weight.

In embodiments, the transvaginal probe for measuring tactile profile of vagina may be configured to obtain tactile patterns at at least two levels of tissue deformation from a portion or the entire length of the anterior and posterior walls and/or the uterus, these levels are defined by the geometry of the front portion and the remainder of the distal portion of the probe. In other embodiments, the probe is shaped and the data processor is configured for obtaining tactile patterns from vagina for at least three levels of tissue deformation—the initial deformation from the front portion of the probe, followed by the maximum deformation from the extrusive portion of the probe, followed by the intermediate deformation by the remaining part of the distal portion of the probe.

BRIEF DESCRIPTION OF DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION OF PREFERRED EMBODIMENTS OF THE INVENTION

Figure 1:
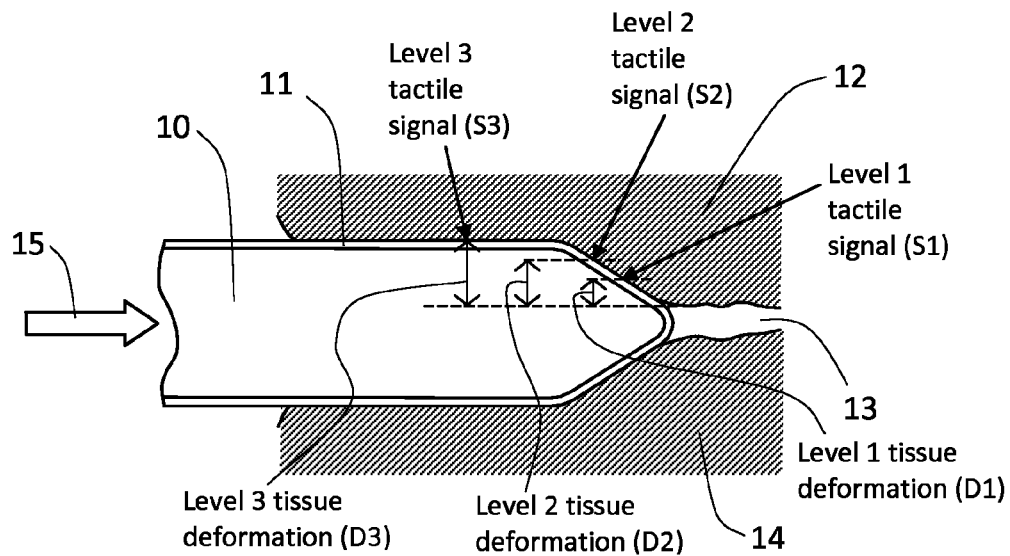
FIG. 1 illustrates a process of insertion of the transvaginal probe into vagina and acquisition of tactile signals for three levels of tissue deformation.

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Specific terms are used in the following description, which are defined as follows: "tactile sensor" is the sensor capable to measure an applied orthogonal force averaged per sensor area or pressure. "Tissue deformation" is used to describe vaginal wall and adjacent structures deformation generally in orthogonal direction from a vaginal canal.

FIG. 1 illustrates a transvaginal probe insertion into vagina and acquisition of one or more tactile patterns from vaginal walls. The transvaginal probe 10 may be covered by a lubricant and equipped with a plurality of tactile sensors 11 forming together a tactile array. The transvaginal probe is shown inserted along the vaginal canal 13 under applied force 15 shown by the arrow to the left end of the probe 10. During the insertion of the transvaginal probe 10, the anterior vaginal wall 12 and opposing posterior vaginal wall 14 are deformed by a front tapered portion of the probe 10, which is shaped to cause progressively increasing deformation levels as the probe 10 is inserted deeper into vagina. Probe location in vagina is calculated during its insertion by analyzing tactile patterns on the tactile sensors 11 on one or both sides of the probe; the deeper the probe is inserted into vagina, the more tactile sensors acquire signals from being in contact with the deformed vaginal wall. Tissue deformation may be described as initial Level 1 tissue deformation D1 for at least one of the opposing vaginal walls such as the anterior vaginal wall, followed by tissue deformation D2 to Level 2, and further increasing tissue deformation D3 to Level 3 at the flat surface of the distal portion of the probe 10 behind the tapered front portion. The tactile sensors 11 may be placed on one or both opposite sides of the transvaginal probe 10 including locations on the front portion of the probe 10 to provide Level 1 tactile signal 51 and Level 2 tactile signal S2. Level 3 tactile signal S3 may be provided by the flat sides of the probe 10. As a result, insertion of the probe 10 provides one, two, three or more levels of vaginal wall deformation and respective tactile signals (or tactile patterns) may be recorded for these tissue deformations. Cumulatively, all tactile patterns recorded by the tactile sensors 11 of the transvaginal probe 10 during the probe insertion into vagina are referred to as a tactile response. These patterns may be recorded during soft tissue deformation and therefore may not be linear. The tissue deformation by the probe 10 may be applied to the opposing walls of the vagina, e.g. anterior versus posterior walls or left wall vs right wall. The probe 10 may have a rectangular, ellipsoidal or circular cross-section. In embodiments, the probe 10 is shaped for atraumatic insertion into vagina and may have a generally rectangular cross-section with rounded edges and angles, so that smaller sides of the probe 10 may be equipped with at least some of the tactile sensors 11. The vaginal tissue deformation during insertion of the transvaginal probe 10 may be used in place of spreading vaginal walls by other probes including those suggested in our previous patent applications. The transvaginal probe of the present invention is generally designed and shaped for easy application of a tissue deformation load directed orthogonally and away from vaginal canal by a simple insertion of the probe into the vaginal canal and towards the uterus assisted with using a lubricated gel. A disposable elastic cover for entire probe can be used for hygiene protection.

Figure 2:
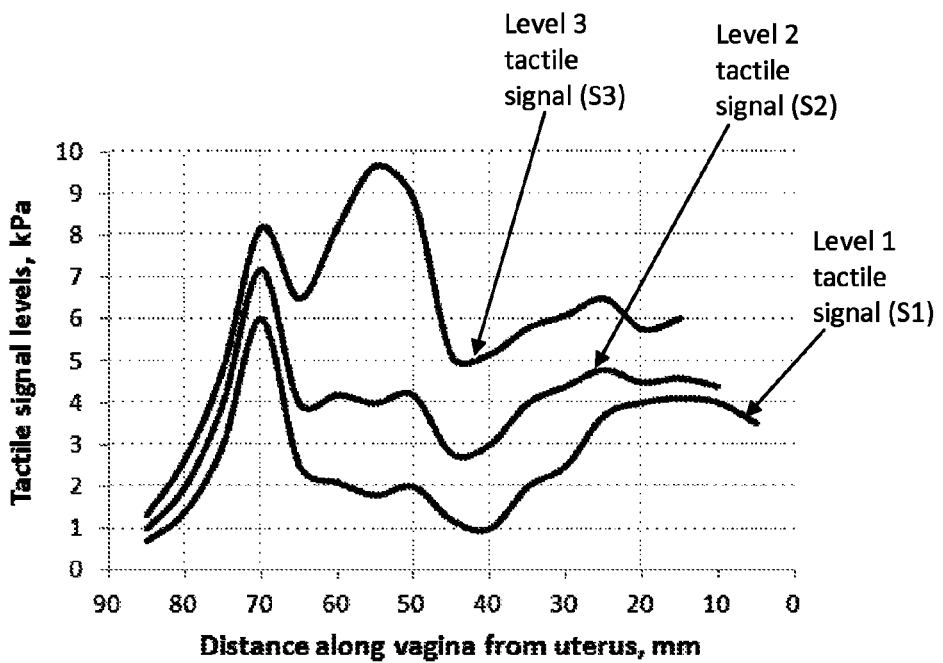
FIG. 2 shows acquired tactile signals at three levels of tissue deformation along vagina.

FIG. 2 illustrates exemplary tactile patterns S1-S3 at three levels of tissue deformation D1-D3 along vagina for the probe design shown in FIG. 1. Elasticity or the capability of substance to be deformed under applied force is generally defined as a ratio of applied stress to resulting strain. In the most basic sense, the tactile signals S1-S3 may be used as a stress while deformations D1-D3 may be used as a strain for calculating vaginal tissue elasticity. The probe 10 may be shaped and tactile sensors 11 may be appropriately placed along the probe 10 in order to provide a constant level of strain during probe insertion. Applying a simple linear mechanical model for soft tissue deformation, Young's modulus may in that case be calculated as a ratio of $(S3-S1)/(D3-D1)$, $(S2-S1)/(D2-D1)$ and $(S3-S2)/(D3-D2)$, all multiplied by a correction factor F, which can be derived from theoretical and experimental data with tissue models. In a more advanced approach, the vaginal tissue deformation may be described by a nonlinear mathematical model accounting for hysteresis. Other methods of mathematical processing of tactile signals are also envisioned to be within the scope of this invention. For example, tactile patterns obtained along a plurality of probe locations along its trajectory of insertion into vagina may be used for determining of one or more 2-D tactile images of vagina as location of each tactile sensor 11 on the probe and the probe geometry and size are all known in advance.

Figure 3:
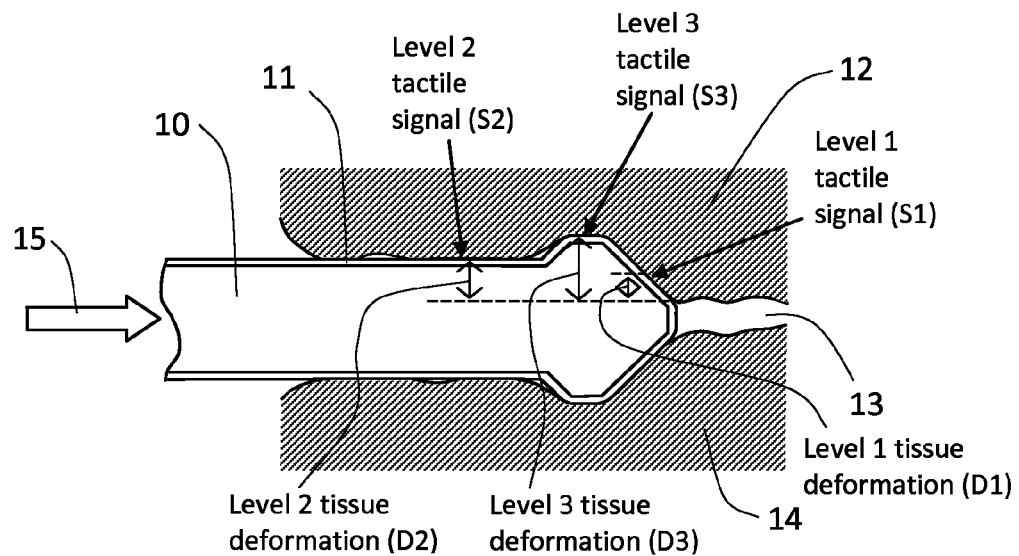
FIG. 3 illustrates insertion of the transvaginal probe with an adjacent extrusive portion into vagina and acquisition of tactile signals for three levels of tissue deformation.

FIG. 3 illustrates insertion of the transvaginal probe 10 into vagina and acquisition of three levels of tactile signals from the vaginal walls according to another embodiment of the invention. The transvaginal probe 10 may be covered by a suitable lubricant and is also equipped with a plurality of tactile sensors 11 positioned along the path aligned with the center of vaginal canal 13. Insertion force 15 is shown by the arrow to the left end of the transvaginal probe 10. During the insertion of the probe 10, the anterior vaginal wall 12 and the opposing posterior vaginal wall 14 are deformed and separated apart by a front portion of the probe 10. Probe insertion causes a progressively increasing deformation from initial Level 1 tissue deformation D1 to the maximum Level 3 tissue deformation D3 by the largest extrusive portion of the probe 10 following the most distal front portion, and then back down to intermediate Level 2 tissue deformation D2 along the flat surface of the probe having a smaller dimension than the extrusive portion behind the front portion. The tactile sensors 11 may be placed on one or both of the opposite sides of the probe along the flat back portion of the probe 10. Tactile sensors 11 may be located at the tapered front portion, extrusive portion or the distal portion of the probe, and provide respective recordings of the initial, maximum and intermediate tactile patterns. As a result, one, two, or three levels of vaginal wall deformation may be obtained along with tactile patterns corresponding to these deformations. All tactile signals recorded by the tactile sensors 11 during the probe 10 insertions into vagina are referred together as a dynamic tactile response because these signals are recorded during examination when soft tissue deformation may not be linear and may have a certain hysteresis. The described deformation is generally applied to the opposing sides of the vagina, e.g. anterior versus posterior walls or left side versus right side. Probe insertion may cause even or uneven tissue deformation in the opposing vaginal walls.

Figure 4:
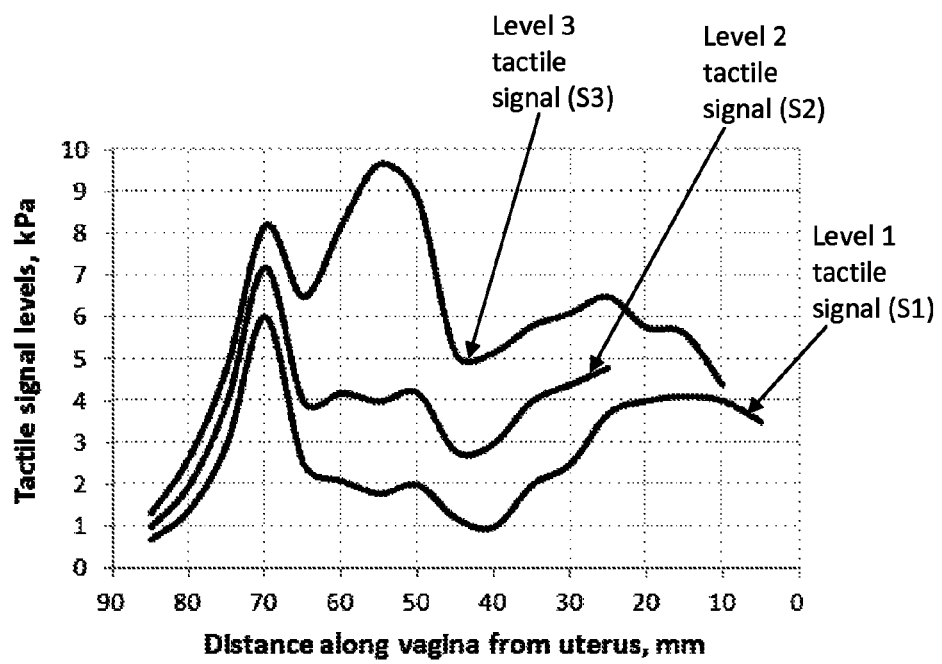
FIG. 4 shows acquired tactile signals at three levels of tissue deformation along vagina.

FIG. 4 illustrates exemplary tactile patterns S1-S3 at three levels of tissue deformation D1-D3 along vagina for the probe shown in FIG. 3. Elasticity is again defined as a ratio of applied stress to resulting strain, in the most basic case S1-S3 over D1-D3. Having the constant strain (which is defined by the probe tapered front portion geometry and by positioning of tactile sensors 11 at least on the front part of the probe to acquire S1) and applying a linear mechanical model for soft tissue behavior, Young's modulus can be calculated as a ratio of (S3−S1)/(D3−D1), (S2−S1)/(D2−D1) and (S3−S2)/(D3−D2) multiplied by the factor F. In embodiments, the tactile signals S1-S3 may be corrected or adjusted by a speed of probe insertion into vagina in order to remove a tangential component from tactile signals; the tissue deformation may also be described by nonlinear model accounting for hysteresis. Other methods of mathematical processing of the tactile signals are also envisioned to be within the scope of this invention. For example, the tactile signals obtained for multiple probe locations during its insertion into vagina may be treated as a 2-D cloud of data and each location on the vaginal wall may be characterized by tactile signals recorded from different tactile sensors at deformation level D2. This approach may be limited as it does not allow elasticity measurement in the vicinity of uterus since only Level 1 tactile signal may be obtained at this location (see FIG. 2).

Figure 5:
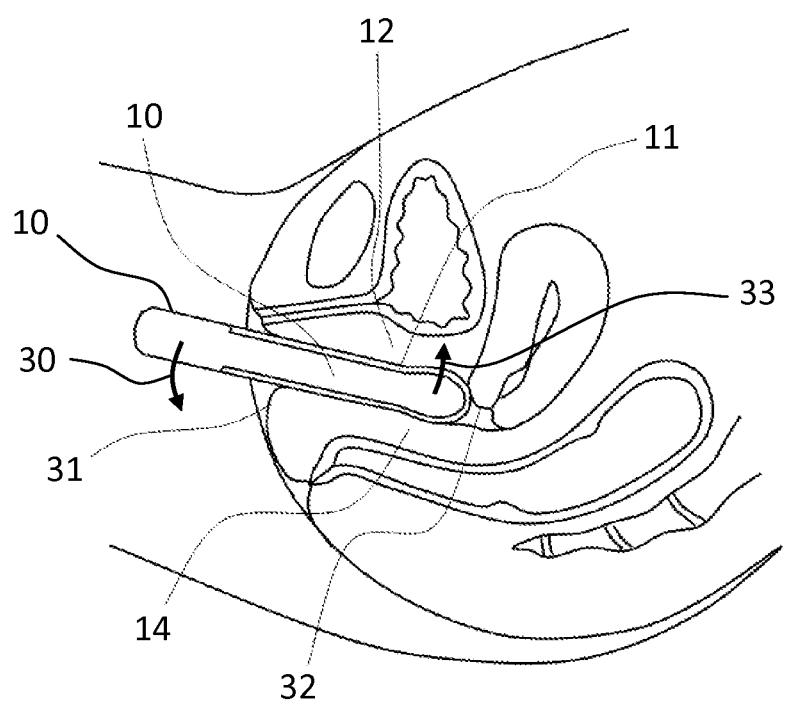
FIG. 5 illustrates transvaginal probe location after its insertion during recording of a static tactile pattern from two opposing vaginal walls and uterus.

FIG. 5 illustrates the transvaginal probe 10 positioned for recording of a static tactile pattern by tactile sensors 11 from two opposing vaginal walls and uterus 32. The static tactile pattern may be recorded for the anterior 12 and the opposing posterior 14 vaginal walls as well as for left and right sides of vagina. Uterus may be used as a reference point in presenting and analyzing static and/or dynamic tactile responses and patterns. Detection of probe position as reaching uterus may be done using the tactile sensors on the front portion of the probe. Reaching uterus may be confirmed when the tactile signals from sensors on the probe tip exceed a certain predetermined threshold. Location of hymen 31 may be used as an additional reference point for tactile profile.

Capture of the static tactile pattern may occur after 3-5 seconds following completion of probe insertion to allow vaginal tissue to get equilibrium in internal stress and strain distribution. To accurately record the static tactile pattern, probe 10 must be held in place without any displacements and keeping the probe orientated in parallel to vagina canal. In embodiments, the patient may be placed in a horizontal position during the probe insertion and capturing the static tactile pattern. Furthermore, the patient may be asked to contract vaginal muscles to enable recording of tactile signals on the flat rigid back surface of the probe 10. The patient may be asked to follow the instruction from a medical professional as to the appropriate time for vaginal muscles contraction.

In embodiments, the probe 10 might be let go and allowed to be freely displaced gravitationally under its own weight as shown by arrows 30 and 33. The transitional tactile response may then be recorded by tactile sensors 11. Usually, vaginal walls have more support around hymen 31 than in the apical anterior part of vagina 12. The probe 10 under its own weight may mostly deform generally the apical anterior part of vagina. A tilt sensor mounted into the probe 10 provides data of its angle changes during transitional probe displacement. Additionally, the probe can be tilted up and down (±20 degrees) by applying elevating, tilting or rotating force relative to the hymen to record deeper transitional tactile response from median and apical anterior and posterior compartments. The recorded transitional tactile response provides vital information about biomechanical conditions of pelvic floor support structures.

Figure 6:
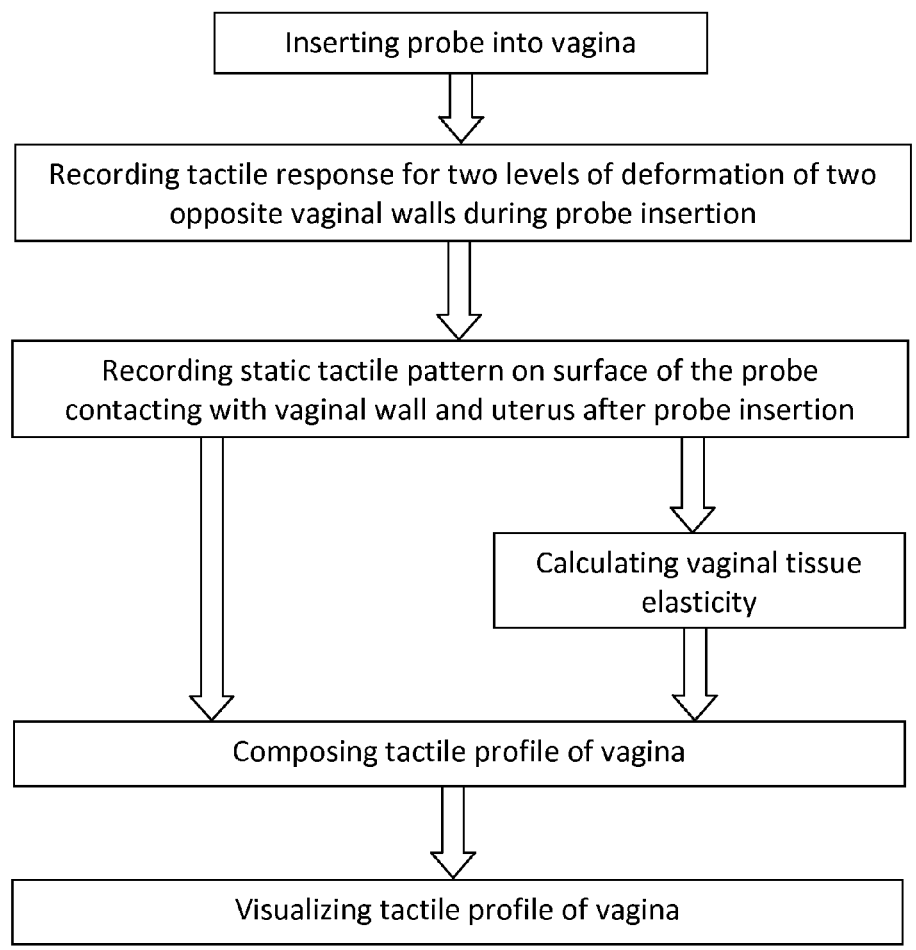
FIG. 6 is a flow chart illustrating one method for measuring tactile profile of vagina.
Figure 9:
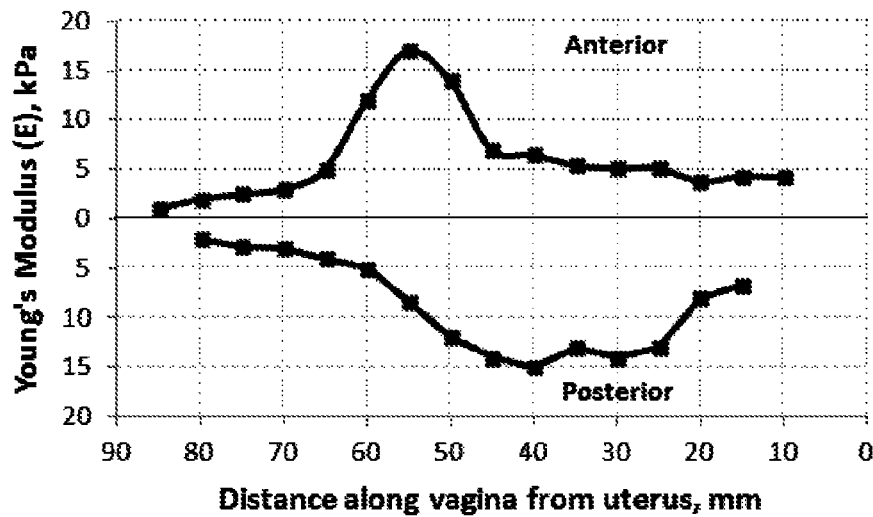
FIG. 9 illustrates an exemplary calculated distribution of Young's modulus of vaginal tissue along vagina.
Figure 10:
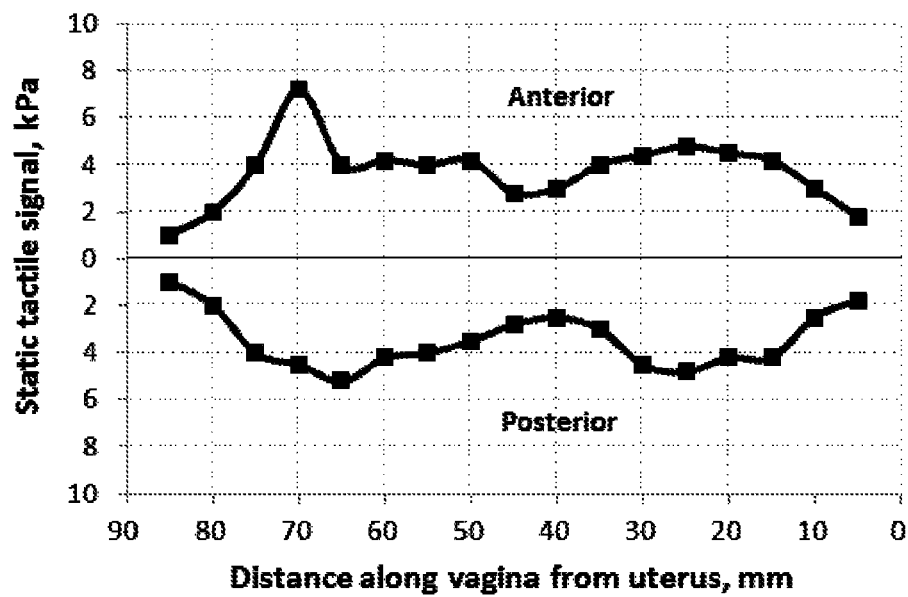
FIG. 10 illustrates an exemplary recorded static tactile pattern from vaginal walls along vagina.

FIG. 6 illustrates one method for measuring tactile profile of vagina comprising the steps of:
  inserting the transvaginal probe into vagina,
  recording a tactile response for at least two levels of deformation on one or both of the two opposing vaginal walls during probe insertion into vagina,
  recording a static tactile pattern from one or both of the two opposing vaginal walls and optionally the uterus after completing the insertion of the probe,
  calculating distribution of vaginal tissue elasticity for a portion or the entire vagina using the tactile response from various parts of the probe recorded for the same location on the vaginal walls,
  composing a vaginal tactile profile from the distribution of vaginal tissue elasticity, static tactile pattern, and pelvic floor muscle strength, and
  visualizing tactile profile of vagina, for example as shown in FIGS. 9 and 10.

Figure 7:
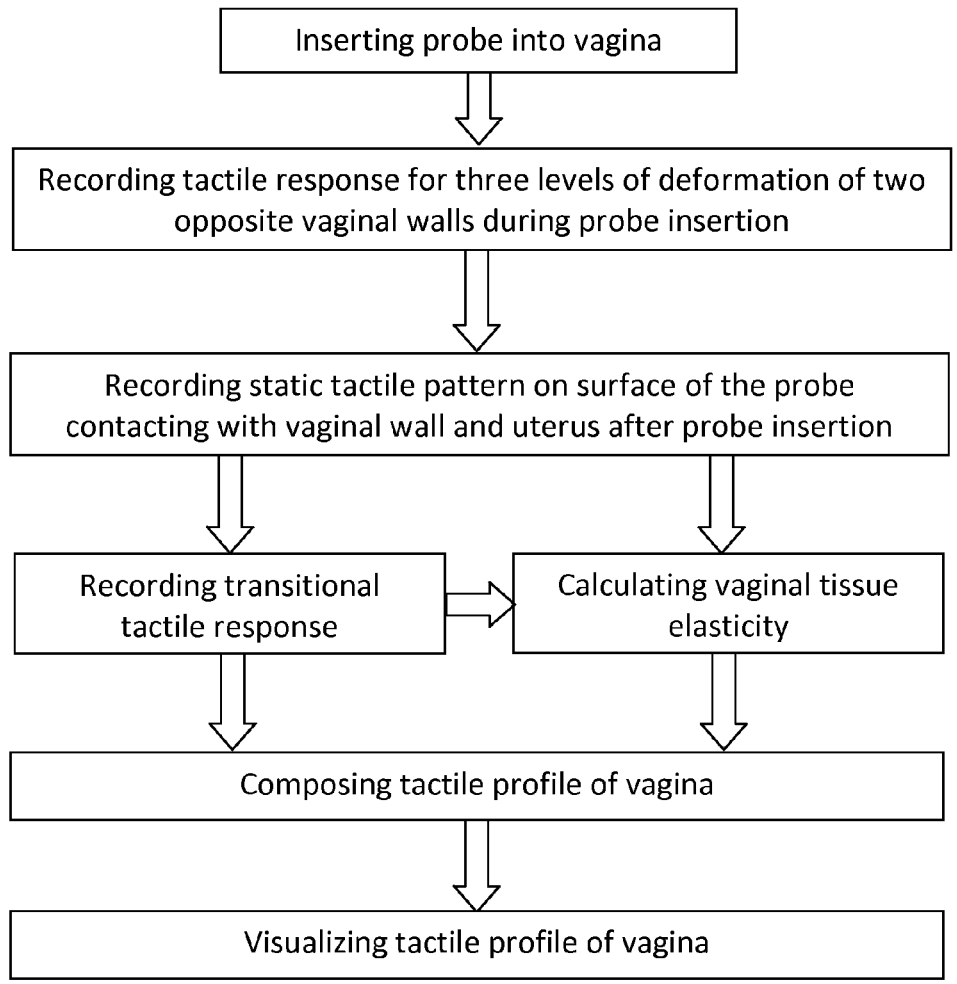
FIG. 7 is a flow chart illustrating another method for measuring tactile profile of vagina including recording of a transitional tactile pattern.

FIG. 7 illustrates another method for measuring a tactile profile of vagina comprising the additional step of recording a transitional tactile response by allowing the probe gravitationally or by applying elevating, tilting or rotating force to deform the median and apical anterior vaginal wall so as to provide additional information about biomechanical conditions of pelvic floor support structures.

In embodiments, additional steps for composing a vaginal tactile profile may include obtaining a recording of tactile patterns when the vaginal muscles are contracted so as to determine pelvic floor muscle strength. Visualizing tactile profile of vagina may be done as shown for example in FIGS. 9 and 10.

Figure 8:
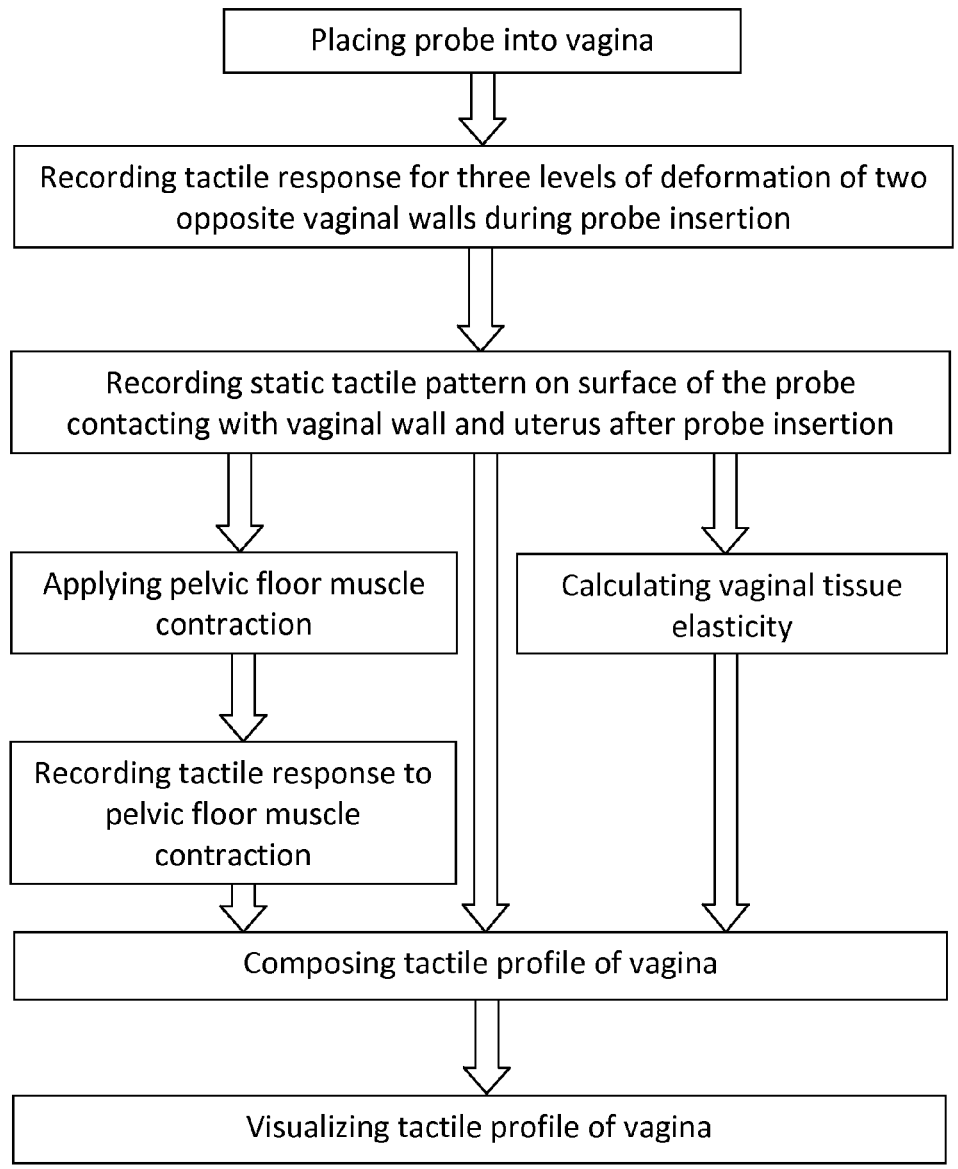
FIG. 8 is a flow chart illustrating another method for measuring tactile profile of vagina including recording of tactile patterns in response to intentional vaginal muscle contraction.

FIG. 8 illustrates another method for measuring a tactile profile of vagina which includes the additional steps of:
  recording a tactile response for three levels of deformation at one or two opposing vaginal walls during probe insertion into vagina,
  recording a static tactile pattern from two opposing vaginal walls and uterus after said probe insertion,
  recording tactile sensor signals on a rigid surface of said probe during vaginal muscle contraction,
  calculating distribution of vaginal tissue elasticity for entire vagina using said tactile response from various portions of the probe including a front part, extrusive parts and a flat part for the same location on a vaginal wall,
  calculating pelvic floor muscle strength from said tactile sensor signals recorded during vaginal muscle contraction, composing a vaginal tactile profile from said distribution of vaginal wall elasticity, static tactile pattern and pelvic floor muscle strength, and visualizing tactile profile of vagina. The step of composing tactile profile of vagina includes data presentation according to FIGS. 9-11.

FIG. 9 illustrates an exemplary calculated distribution of Young's modulus of vaginal tissue along vagina for anterior and posterior vaginal compartments. The Young's modulus is calculated as a ratio of (S3−S1)/(D3−D1), (S2−S1)/(D2−D1) and (S3−S2)/(D3−D2) multiplied by the factor F, where S1-S3 are tactile signals and D1-D3 are respective tissue deformations (see FIGS. 2 and 4).

FIG. 10 illustrates an exemplary recorded static tactile pattern from vaginal walls along vagina for anterior and posterior vaginal compartments (see FIG. 5 description for details).

Figure 11:
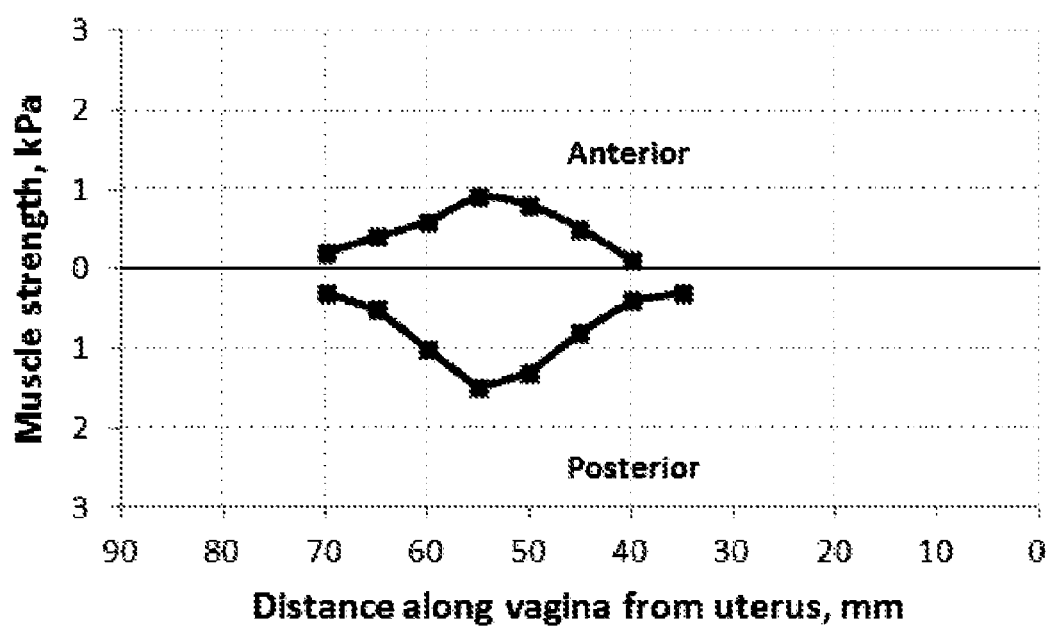
FIG. 11 illustrates an exemplary calculated muscle strength along vagina.

FIG. 11 illustrates an exemplary calculated vaginal muscle strength profile along vagina for anterior and posterior vaginal compartments (see FIG. 5 description for details).

Figure 12:
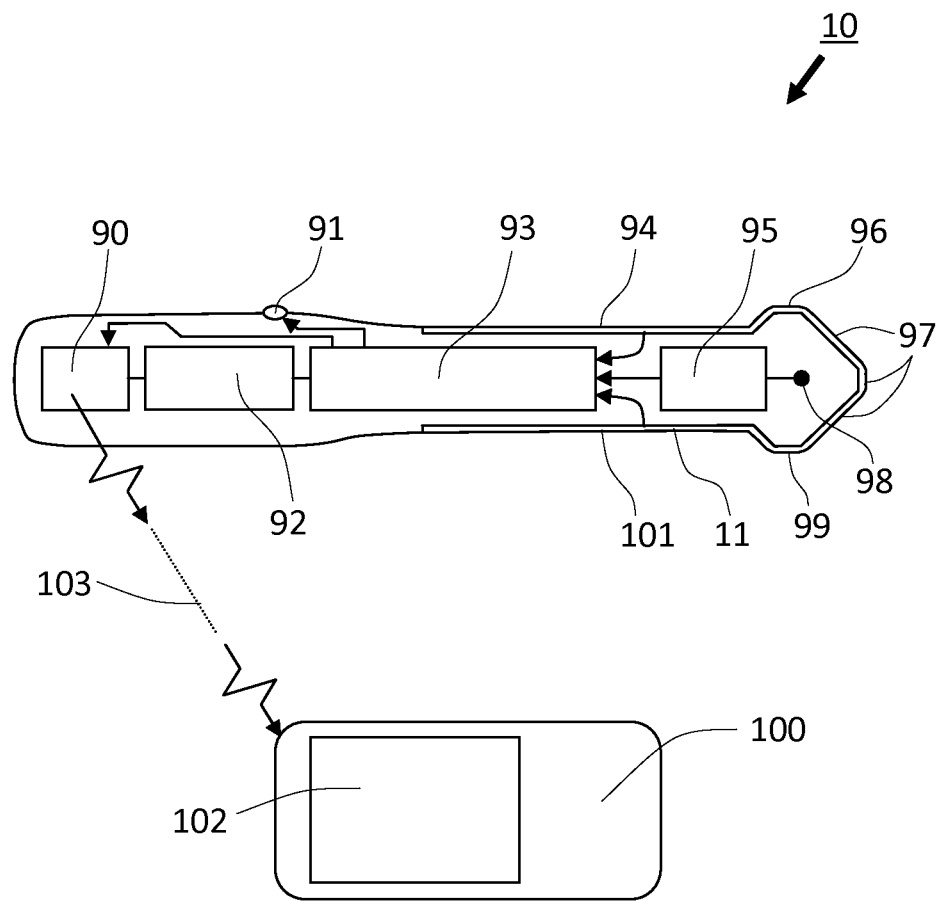
FIG. 12 presents a schematic diagram of one embodiment of the transvaginal probe with an external data processor.
Figure 15:
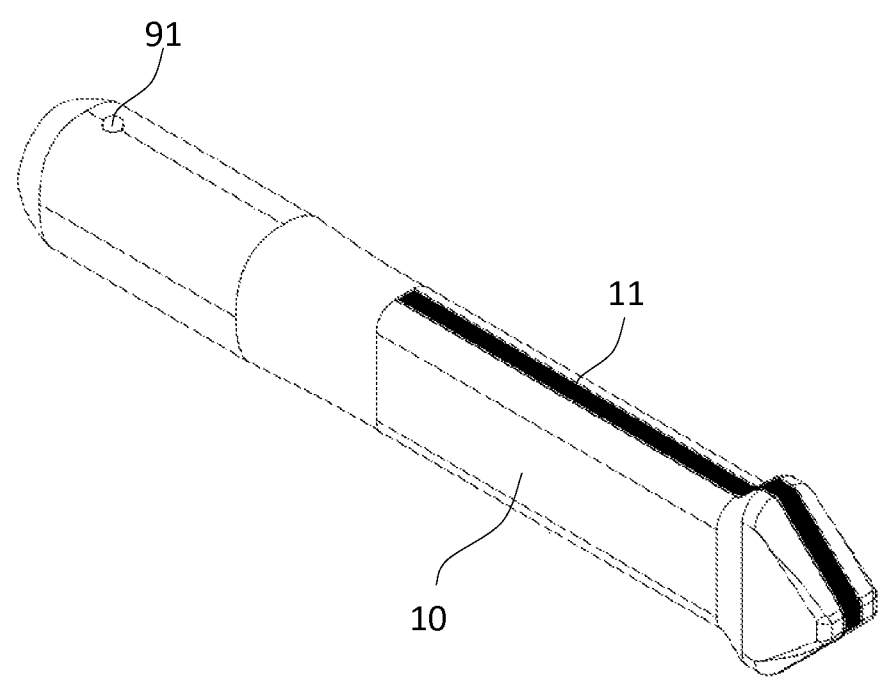
FIG. 15 presents a perspective view of the transvaginal probe as depicted in FIG. 12.

FIGS. 12 and 15 present a schematic diagram and a perspective view of the transvaginal probe 10 with its internal components and a controller including a data processor 100. In embodiments, the data processor 100 may be incorporated with the probe 10 or be external to its housing. The probe 10 for measuring tactile profile of vagina generally includes a tactile sensor array 11 configured to obtain simultaneously tactile signals at one or more levels of tissue deformation from a portion or the entire length of anterior and posterior vaginal walls and optionally the uterus, a light indicator 91 configured to provide a confirmation signal indicating that the probe reached uterus. The indicator may be turned on when the tactile pattern on the front portion of the probe is detected as exceeding a predetermined threshold as may be the case when the probe cannot be advanced any further. Reaching the uterus may be used as a reference point in composing a vaginal tactile profile.

The probe 10 may further include at least one temperature sensor 98 and a micro heater with a heater controller 95 configured to increase the surface temperature of tactile sensors to within 5 degrees or better from body temperature of 37 degree Celsius. Heating up the surface of the probe may not only improve the comfort of the vagina examination but also avoid heat expansion of the tactile sensors while inside the vagina which may cause data distortion. The probe may further include data acquisition electronics 93, a rechargeable battery 92, and a port 90 for communicating with external data processor 100. The data processor 100 may include a display 102 to present examination results with vaginal tactile profiles.

The probe 10 may be shaped for atraumatic insertion into vagina with two flat parts 94 and 101 shaped for contact with two opposing vaginal walls and providing intermediate level 2 deformation (see FIG. 1). The probe 10 may also have two extrusive parts 96 and 99 to contact with two opposing vaginal walls providing maximal level 3 deformation (see FIG. 1). The probe 10 may further have a front tapered portion to contact with two opposing vaginal walls and uterus providing initial level 1 deformation (see FIG. 1). Tactile sensors 11 may cover some or all of these listed parts (94, 96, 97, 99 and 101) of the probe 10. The data acquisition electronics 93 may include a memory element for storing acquired tactile signals before transmission to the data processor 100. Also, the data acquisition electronics 93 may include a tilt sensor (such as an accelerometer) to provide angle orientation data relative to the Earth horizon.

Communication and data transfer between the probe 10 and data processor 100 may be wireless as shown by the dotted line 103. Alternatively, data transfer between the probe 10 and data processor 100 may be provided by a wire connection; in this case there is no need for a rechargeable battery 92 to be located inside the probe 10. In embodiments, a computer may be used as a data processor 100. Appropriate software may be developed to support at least three operational modes:

a. data acquisition mode,
b. data management mode, and
c. device management mode.

The software may allow for storing the data in a digital format, visualization of the tactile profile of vagina, comparison of multiple vaginal tactile profiles, software updates and examination data transmission over the Internet. The processor 100 and the display 102 may be configured for a comparative analysis of acquired vaginal tactile profile with a variety of vaginal tactile profiles recorded for a defined population with known clinical status so as to assist in detecting a disease.

Figure 13:
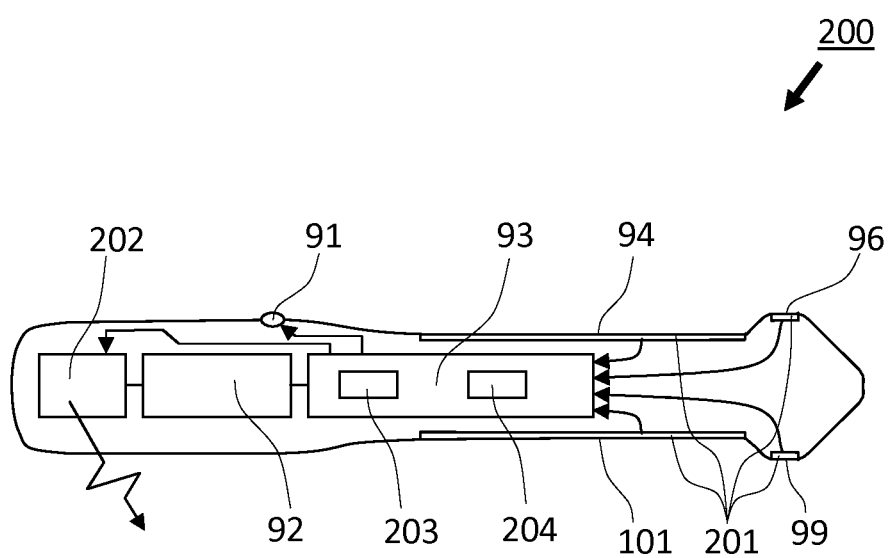
FIG. 13 presents a schematic diagram of another embodiment of the transvaginal probe.

FIG. 13 presents a schematic diagram of an alternative transvaginal probe 200 for measuring tactile profile of vagina, which comprises a tactile sensor array 201 for recording tactile signals at two levels of tissue deformation from at least a portion of the anterior and/or posterior vaginal walls, a light indicator 91 to provide signal indicating the probe operational status, a data acquisition electronics 93, a rechargeable battery 92, and a wireless communication port 202 communicating with external data processor such as a computer, tablet computer or smart phone. The probe 200 is shaped to have two flat parts 94 and 101 suitable to contact with two opposing vaginal walls providing level 2 deformation (see FIG. 3) and two extrusive parts 96 and 99 to contact with two opposing vaginal walls providing level 3 deformation (see FIG. 3). Tactile sensors 201 may cover some or all of the probe parts 94, 96, 99 and 101. The data acquisition electronics 93 includes a memory 203 for storing acquired tactile signals before transmission to the data processor. The data acquisition electronics 93 further includes an accelerometer 204 which is used as a tilt sensor and as a shock sensor to detect high probe impact, for example if the probe 200 is accidently dropped on a floor.

Figure 14:
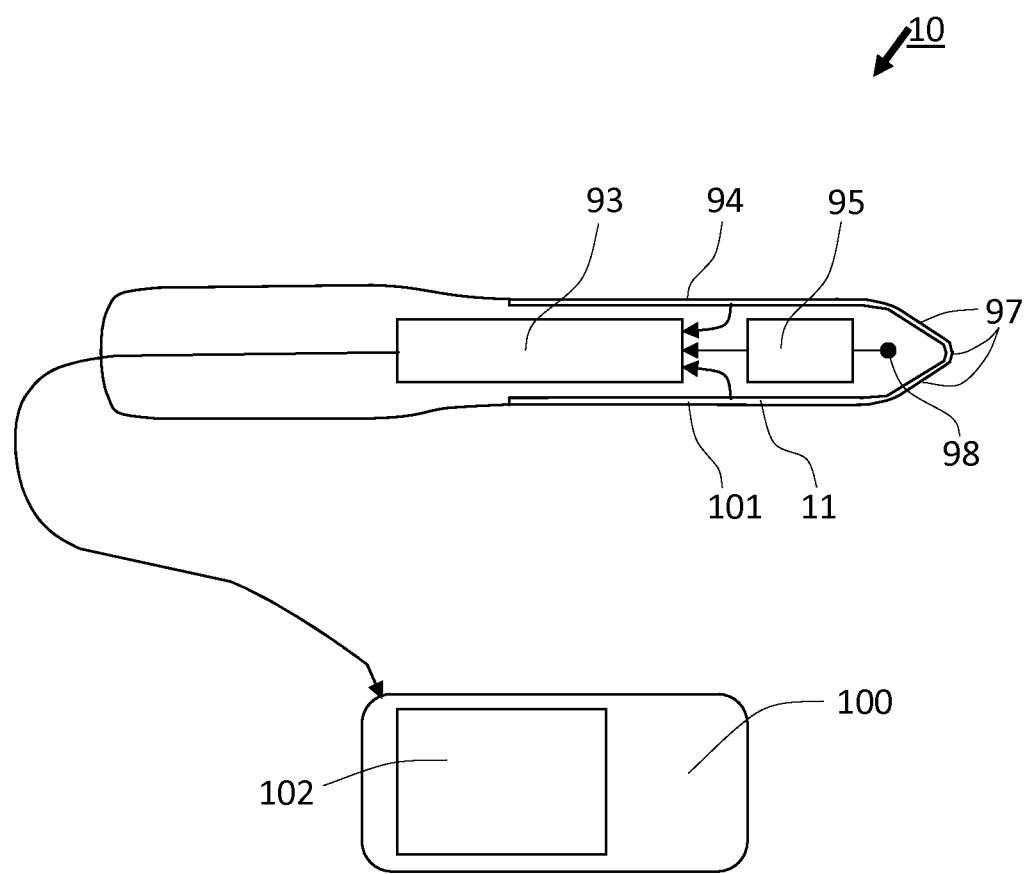
FIG. 14 presents a schematic diagram of yet another embodiment of the transvaginal probe.
Figure 16:
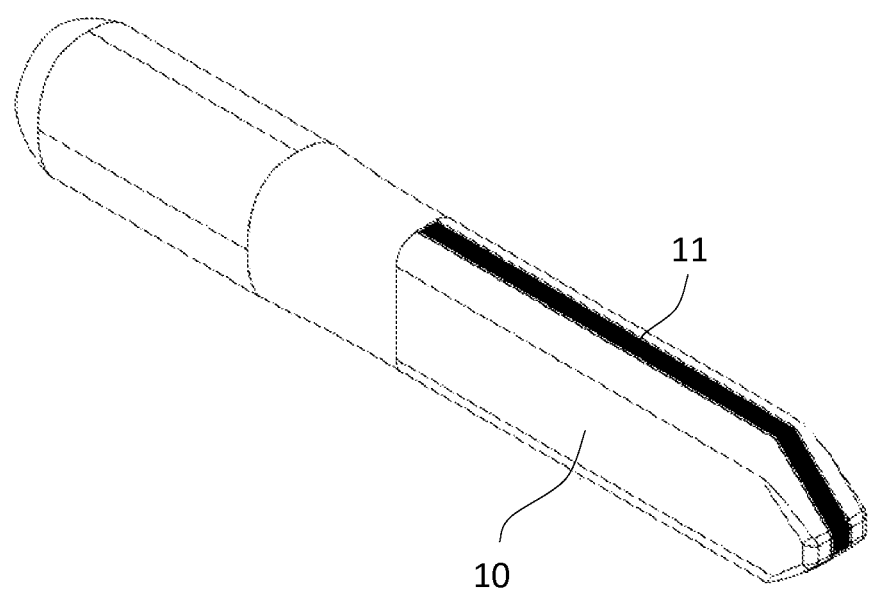
FIG. 16 presents a perspective view of the transvaginal probe as shown in FIG. 14.

FIGS. 14 and 16 present a schematic diagram and a perspective view of a transvaginal probe 10 with its internal components according to that previously described. The probe 10 comprises a tactile sensor array 11 configured to record tactile signals at least at three levels of tissue deformation from part of entire length of vagina and uterus, a temperature sensor 98, a micro heater with heater controller 95 to support temperature of tactile sensors about 37±5 degree Celsius with the purpose of improving tactile sensor accuracy, and a data acquisition electronics 93 communicating with the external data processor 100. A number of temperature sensors may be increased from 1 up to 10 sensors (for different zones) and a number of heaters also may be increased accordingly to provide for an even temperature distribution along the probe surface. Furthermore, the data processor 100 may include a display 102 to present examination data with vaginal tactile profiles. The probe 10 may have two flat parts 94 and 101 to contact with two opposing vaginal walls providing level 3 deformation (see FIG. 1) and a front part to contact with two opposing vaginal walls and uterus for providing level 1 and level 2 deformation (see FIG. 1). Tactile sensors 11 may cover some or all listed parts (94, 97, and 101) of the probe 10. Data acquisition electronics 93 may further include a tilt sensor to provide probe angle orientation data relative to the Earth horizon. Data transfer between the probe 10 and data processor 100 may be provided by a wired or wireless connection.

The herein described subject matter sometimes illustrates different components or elements contained within, or connected with, different other components or elements. It is to be understood that such depicted architectures are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for determining a tactile profile of vagina, said method comprising the steps of:
    (a) inserting a transvaginal probe into said vagina along a vaginal canal to separate apart two opposing vaginal walls thereof, whereby causing vaginal tissue deformation away from said vaginal canal,
    (b) recording a tactile response simultaneously for at least two levels of said vaginal tissue deformation over at least a portion of said transvaginal probe in contact with at least one of said two opposing vaginal walls while inserting said probe into said vagina,
    (c) determining probe location in said vagina based on presence or absence of said tactile response along said probe, and
    (d) determining said tactile profile of said vagina based on said tactile response and said probe location.

2. The method as in claim 1, wherein steps (b) and (c) are performed during said insertion in step (a) of said transvaginal probe into said vagina and said step (b) further including recording of a static tactile pattern after said insertion is complete for at least one of said two opposing vaginal walls.

3. The method as in claim 2, wherein said step (b) further including recording of a transitional tactile pattern by elevating said transvaginal probe away from said vaginal canal by an angle not exceeding 20degrees while inside said vagina wherein causing said transvaginal probe to further deform said vaginal tissue, whereby facilitating a comprehensive characterization of biomechanical conditions of pelvic floor support structures.

4. The method as in claim 3, wherein said step (d) further including determining of vaginal tissue elasticity along at least a portion of said vagina based on said tactile profile and said transitional tactile pattern.

5. The method as in claim 4, wherein said step (d) further including calculating of a distribution of said vaginal tissue elasticity along at least a portion of said vagina and calculating said tactile profile of said portion of said vagina based on said distribution, said static tactile pattern and said transitional tactile pattern are all recorded for that same portion of said vagina.

6. The method as in claim 1, wherein determining of vaginal tissue elasticity in step (d) for at least one location in said vagina is based on a ratio of a tactile pattern change to a deformation change, said tactile pattern change and said deformation change are determined for the same location in said vagina.

7. The method as in claim 1, wherein said two opposing vaginal walls are an anterior vaginal wall and a posterior vaginal wall.

8. The method as in claim 1, wherein said two opposing vaginal walls are a left vaginal wall and a right vaginal wall.

9. The method as in claim 2, wherein said transvaginal probe is inserted into said vagina until reaching said uterus, said uterus is then used in steps (b) through (d) as a reference point for determining said tactile profile for said two opposing vaginal walls.

10. The method as in claim 1 further including step (e) of comparing said tactile profile to tactile profiles obtained from a group of patients with known clinical conditions so as to detect a presence or an absence of a disease.

11. The method as in claim 1, wherein said step (b) further including recording of said tactile response for at least three deformation levels of the same portion of said vagina, starting with an initial deformation level, followed by a maximum deformation level, followed by an intermediate deformation level, said intermediate deformation level being less than said maximum deformation level.

12. The method as in claim 1, wherein said step (b) of recording said tactile response is conducted during contraction of vaginal muscles, said step (d) further including determining pelvic floor muscle strength.

13. A transvaginal probe for determining a tactile profile of vagina, said transvaginal probe comprising:
    a probe housing with a front portion suitably shaped for atraumatic insertion into a vaginal canal and for separating two opposing vaginal walls thereof,
    a plurality of tactile sensors forming together a tactile array, said plurality of tactile sensors are located over at least a portion of said probe housing in a predefined relationship of sensor positions to each other and to said probe housing, said plurality of tactile sensors are configured to record a tactile response of said vagina when at least some of said tactile sensors are in contact with at least one of said two opposing vaginal walls as a result of inserting said transvaginal probe into said vagina, and
    wherein said probe housing includes a distal portion having parallel side walls and terminated with said front portion, said front portion is tapered, said tactile sensors of said tactile array are placed along said tapered front portion and along said parallel side walls of said distal portion, and
    a controller including a data processor with a recorder of said tactile response from each of said plurality of tactile sensors, said data processor is also configured for determining said tactile profile of said vagina based on said tactile response, said known sensor positions and a probe location in said vagina, said probe location is determined based on how many tactile sensors of said tactile array are in contact with said vaginal walls.

14. The transvaginal probe as in claim 13, wherein said data processor is configured to detect said tactile response exceeding a predetermined threshold for said front portion, whereby indicating reaching of a uterus by said transvaginal probe.

15. The transvaginal probe as in claim 13 further including a heating system including at least one temperature sensor and at least one heater, said controller is configured to cause said heating system to maintain an exterior surface of at least said front portion of said probe housing at a surface temperature deviating from 37 degrees Celsius by not more than 5 degrees Celsius.

16. The transvaginal probe as in claim 13 further equipped with a display for presenting said tactile profile of said vagina.

17. The transvaginal probe as in claim 13, wherein said distal portion further includes an extrusive portion adjacent to said front tapered portion, said extrusive portion having a maximum outside dimension greater than a maximum outside dimension of any other part of said distal portion, said extrusive portion including at least some tactile sensors from said tactile array, said data processor is configured to record said tactile response at a maximum deformation level when said portion of said vagina is in contact with sais extrusive portion of said probe housing.

18. The transvaginal probe as in claim 13 further including a tilt sensor for detecting an angular position of said probe relative to an Earth horizon.

\* \* \* \* \*